US008785682B2

(12) United States Patent
FitzGerald et al.

(10) Patent No.: US 8,785,682 B2
(45) Date of Patent: Jul. 22, 2014

(54) TETRANOR PGDM: A BIOMARKER OF PGD$_2$ SYNTHESIS IN VIVO

(75) Inventors: Garret A. FitzGerald, Wayne, PA (US); Wenliang Song, Philadelphia, PA (US); John A. Lawson, Penn Valley, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 624 days.

(21) Appl. No.: 12/680,153

(22) PCT Filed: Sep. 29, 2008

(86) PCT No.: PCT/US2008/078141
§ 371 (c)(1),
(2), (4) Date: Mar. 25, 2010

(87) PCT Pub. No.: WO2009/043015
PCT Pub. Date: Apr. 2, 2009

(65) Prior Publication Data
US 2010/0209962 A1   Aug. 19, 2010

Related U.S. Application Data

(60) Provisional application No. 60/995,524, filed on Sep. 27, 2007.

(51) Int. Cl.
*C07C 61/06* (2006.01)
*C07C 59/11* (2006.01)
*G01N 33/53* (2006.01)
*G01N 33/567* (2006.01)

(52) U.S. Cl.
CPC .................. *C07C 61/06* (2013.01); *C07C 59/11* (2013.01); *G01N 33/53* (2013.01); *G01N 33/567* (2013.01)
USPC ........................................... 562/504; 435/7.2

(58) Field of Classification Search
CPC ........ C07C 61/06; C07C 59/11; G01N 33/53; G01N 33/567
USPC .......................................... 562/504; 435/7.2
See application file for complete search history.

(56) References Cited

U.S. PATENT DOCUMENTS 5,986,094 A    11/1999  Ghoshal et al.

FOREIGN PATENT DOCUMENTS

EP           1338594 A1    8/2003

OTHER PUBLICATIONS

Ellis et al Journal of Biological Chemistry 1979, 254(10), 4152-4163.*
Bell-Parikh et al., "Biosynthesis of 15-deoxy-$\Delta^{12,14}$-PGJ$_2$ and the ligation of PPARγ." *J Clin Invest.*, (2003) 112:945-955.
Bochenek et al., "A controlled study of 9α, 11β-PGF$_2$ (a prostaglandin D$_2$ metabolite) in plasma and urine of patients with bronchial asthma and healthy controls after aspirin challenge." *J Allergy Clin Immunol.*, (2003) 111:743-749.
Bochenek et al., "Plasma 9α, 11β-PGF$_2$, a PGD$_2$ metabolite, as a sensitive marker of mast cell activation by allergen in bronchial asthma." *Thorax*, (2004) 59:459-464.
Bushfield et al., "Inhibition of platelet-activating-factor-induced human platelet activation by prostaglandin D$_2$." *Biochem. J.* (1985) 232:267-271.
Catella et al., "11-Dehydrothromboxane B$_2$: A quantitive index of thromboxane A$_2$ formation in the human circulation." *Proc. Natl. Acad. Sci. USA* (1986) 83:5861-5865.
Cheng et al., "Antagonism of the prostaglandin D$_2$ receptor 1 suppresses nicotinic acid-induced vasodilation in mice and humans. *Proc. Natl. Acad. Sci. USA* (2006) 103(17):6682-6687.
Cheng et al., "Cyclooxygenases, microsomal prostaglandin E synthase-1, and cardiovascular function." *J. Clin. Invest.* (2006) 116(5):1391-1399.
Dahlen et al., "Monitoring mast cell activation by prostaglandin D$_2$ in vivo." *Thorax* (2004) 59:453-455.
Ellis et al., "Metabolism of prostaglandin D$_2$ in the Monkey." *J. Biol. Chem.* (1979) 254(10); 4152-4163.
FitzGerald et al. "Endogenous biosynthesis of prostacyclin and thromboxane and platelet function during chronic administration of aspirin in man." *J. Clin. Invest.* (1983) 71:676-688.
Forman et al., "15-deoxy-$\Delta^{12,14}$-Prostaglandin J$_2$ is a ligand for the adipocyte determination factor PPARγ." *Cell* (1995) 83:803-812.
Fries et al., "Marked interindividual variability in the response to selective inhibitors of cyclooxygenase-2." *Gastroenterology* (2006) 130:55-64.
Gilroy et al., "Inducible cyclooxygenase may have anti-inflammatory properties." *Nat. Med.* (1999) 5(6):698-701.
Ito et al., "Problems in production of prostaglandin D2-specific antibody." *Eicosanoids* (1988) 1(2):111-116 Abstract Only.
Lawson et al., "Isoprostanes: formation, analysis and use as indices of lipid peroxidation in vivo." *J. Biol. Chem.* (1999) 274(35):24441-24444.
Liston et al., "Metabolic fate of radiolabeled prostaglandin D$_2$ in a normal human male volunteer." *J. Biol. Chem.* (1985) 260(24):13172-13180.
Matsuoka et al., "Prostaglandin D$_2$ as a mediator of allergic asthma." *Science* (2000) 287:2013-2017.
McAdam et al., "Effect of regulated expression of human cyclooxygenase isoforms on eicosanoid and isoeicosanoid production in inflammation." *J. Clin. Inv.* (2000) 105(10):1473-1482.
McAdam et al., "Systemic biosynthesis of prostacyclin by cyclooxygenase (COX)-2: the human pharmacology of a selective inhibitor of COX-2." *Proc. Natl. Acad. Sci. USA* (1999) 96:272-277.
Morrow et al., "Improved diagnosis of mastocytosis by measurement of the major urinary metabolite of prostaglandin D$_2$." *Soc. Invest. Derm.* (1995) 104:937-940.
Morrow et al., "Release of markedly increased quantities of prostaglandin D2 in vivo in humans following the administration of nicotinic acid." *Prostaglandins* (1989) 38(2):263-274.
Nagata et al., "CRTH2, an orphan receptor of T-helper-2-cells, is expressed on basophils and eosinophils and responds to mast cell-derived factor(s)." *FEBS Letters* (1999) 459:195-199.

(Continued)

*Primary Examiner* — Yevegeny Valenrod
(74) *Attorney, Agent, or Firm* — Saul Ewing, LLP; Kathryn Doyle

(57) ABSTRACT

The present invention relates to a prostaglandin D$_2$ metabolite, derivatives thereof, compositions comprising the metabolite, and an antibody that specially binds to the metabolite. Methods of use are also provided.

4 Claims, 7 Drawing Sheets

(56) References Cited

OTHER PUBLICATIONS

Nagata et al., "Selective expression of a novel surface molecule by human Th2 cell in vivo." *J Immunol.* (1999) 162:1278-1286.

O'Sullivan et al., "Increased urinary excretion of the prostaglandin D2 metabolite 9α, 11β-prostaglandin $F_2$ after aspirin challenge supports mast cell activation in aspirin-induced airway obstruction." *J. Allergy Clin Immunol.* (1996) 98:421-432.

O'Sullivan et al., "Analyses of prostaglandin $D_2$ metabolites in urine: comparison between enzyme immunoassay and negative ion chemical ionisation gas chromatography-mass spectrometry." *Prostaglandins & Other Lipid Mediators* (1999) 57:149-165.

Song et al., "Tetranor PGDM, an abundant urinary metabolite reflects biosynthesis of prostaglandin $D_2$ in mice and humans." *J Biol Chem.* (2008) 283(2):1179-1188.

Song et al., "Noninvasive assessment of the role of cyclooxygenases in cardiovascular health: A detailed HPLC/MS/MS method." *Methods in Enzymology* (2007) vol. 433, E-published online.

Watanabe et al., "Stereospecific conversion of prostaglandin $D_2$ to (5Z,13E)-(15S)-9α,-11β,15-trihydroxyprosta-5,13-dien-1-oic acid (9α,11β-prostaglandin $F_2$) and of prostaglandin $H_2$ to prostaglandin $F_{2α}$ by bovine lung prostaglandin F synthase." *Proc. Natl. Acad. Sci. USA* (1986) 83:1583-1587.

\* cited by examiner

A tetranor PGDM in mouse urine

B tetranor PGDM in PGD$_2$ infused mouse urine

C tetranor PGDM in human urine

TETRANOR PGDM: A BIOMARKER OF PGD$_2$ SYNTHESIS IN VIVO

CROSS-REFERENCE TO RELATED APPLICATIONS

This is a National Stage application of PCT International Application No. PCT/US2008/078141, filed Sep. 29, 2008, which in turn claims the benefit pursuant to 35 U.S.C. §119(e) of U.S. Provisional Application No. 60/995,524, filed on Sep. 27, 2007, which is hereby incorporated by reference in its entirety herein.

STATEMENT REGARDING FEDERALLY SPONSORED RESEARCH OR DEVELOPMENT

This invention was supported in part by funds obtained from the U.S. Government (National Institutes of Health grant number HL-83799), and the U.S. Government therefore has certain rights in the invention.

BACKGROUND OF THE INVENTION

Prostaglandin D$_2$ (PGD$_2$) is formed from the PGH$_2$ cyclooxygenase (COX) product of arachidonic acid by the action of either a lipocalin (L)-like or hemopoietic (H) PGD synthase (Urade et al., 2000, Vitamins and Hormones, 58: 89-120). Both COX enzymes (COX 1 and COX 2) may form PGD$_2$ in vitro, but it is unclear which COX and PGDS enzymes predominate under varied conditions in vivo.

Suppression of PGD$_2$ has been implicated in the bronchoconstriction of aspirin-evoked asthma (O'Sullivan et al., 1996, J Allergy Clin Immunol, 98: 421-432; Bochenek et al., 2003, J Allergy Clin Immunol, 111: 743-749) and release of PGD$_2$ mediates the facial flushing and vascular instability of systemic mastocytosis (Roberts et al., 1980, N Engl J Med., 303: 1400-1404). PGD$_2$ relaxes vascular smooth muscle cells in vitro and its release by dermal dendritic cells contributes to the facial flushing, which complicates administration of the hypolipidemic drug, niacin (Morrow et al., 1989, Prostaglandins, 38: 263-274). PGD$_2$ mediates its effects via activation of D prostanoid receptors (DPs). DP1, a member of the prostanoid family of G protein coupled receptors (GPCRs), mediates the vasorelaxant and bronchodilator effects (Williams et al., 1977, Nature, 270: 530-532; Matsuoka et al., 2000, Science, 287: 2013-2017). DP2, a GPCR of the fMLP receptor subfamily, regulates Th1 and Th2 switching in lymphocytes (Nagata et al., 1999, J Immunol, 162: 1278-1286) and is also expressed on eosinophils and basophils (Nagata et al., 1999, FEBS Lett., 459: 195-199).

Recent interest in PGD$_2$ has been prompted by the use of DP1 blockade as an adjunct to niacin therapy (Cheng et al., 2006, Proc Natl Acad Sci USA, 103: 6682-6687) and by the potential role of PGD$_2$ and its metabolites in the resolution of inflammation (Gilroy et al., 1999, Nat Med, 5: 698-701). However, DP1 is expressed on human platelets and its activation in vitro results in a cyclic-AMP-dependent inhibition of platelet function (Oelz et al., 1977, Prostaglandins, 13: 225-234; Bushfield et al., 1985, Biochem J, 232: 267-271). Nothing is known about the formation of PGD$_2$ or the consequences of its inhibition in hyperlipidemic patients. Aside from a potential role in cardiovascular disease, PGD$_2$ may be of importance in the resolution of inflammation. A potential metabolite of PGD$_2$, 15-deoxy $\Delta^{12,14}$PGJ$_2$, has been postulated to activate PPARγ (Forman et al., 1995, Cell, 83: 803-812) and promote resolution of an inflammatory infiltrate (Gilroy et al., 1999, Nat Med, 5: 698-701). However, it remains to be determined by physicochemical methodology whether formation of 15-deoxy $\Delta^{12,14}$PGJ$_2$ is indeed augmented during the resolution of human inflammation, and although it can activate PPARγ, the concentrations required are unlikely to be attained in vivo (Bell-Parikh et al., 2003, J Clin Invest, 112: 945-955).

Attempts to assess the biosynthesis of PGD$_2$ have been constrained by a paucity of relevant methodology. Aside from asthma and mastocytosis (O'Sullivan et al., 1996, J Allergy Clin Immunol, 98: 421-432; Bochenek et al., 2003, J Allergy Clin Immunol, 111: 743-749; Roberts et al., 1980, N Engl J Med., 303: 1400-1404), little information on biosynthesis of PGD$_2$ in humans has been acquired. Given the evanescence of primary PGs, biosynthesis is classically estimated by measurement of metabolites (McAdam et al., 1999, Proc Natl Acad Sci USA., 96: 272-277; Catella et al., 1986, Proc Natl Acad Sci USA., 83: 5861-5865). However, no metabolites of PGD$_2$ have been reported in mouse, preventing assessment of biosynthetic response to experimental manipulation in that species. Initial attempts at assay development in humans have focused on 11β-PGF$_{2\alpha}$ formed from PGD$_2$ by bovine PGF synthase (Watanabe et al., 1986, Proc Natl Acad Sci USA., 83: 1583-1587) and 2,3-dinor-11β-PGF$_{2\alpha}$. Both are formed as minor urinary metabolites in monkeys and in a human volunteer following infusion of radiolabelled PGD$_2$ (Liston et al, 1985, J Biol Chem, 260: 13172-13180). However, paired analysis of 11β-PGF$_{2\alpha}$ by gas chromatography mass spectrometry and a commercially available immunoassay revealed poor concordance in the urine of patients with asthma (Misso et al., 2004, Clin Exp Allergy, 34: 624-631; Bochenek et al., 2004, Thorax., 59: 459-464). Quantitative analysis of another major F ring metabolite, 9α,11β-dihydroxy-15-oxo-2,3,18,19-tetranorprost-5-ene-1,20-dioic acid, has been reported in human plasma and urine (Morrow et al., 1995, J Invest Dermatol, 104: 937-940).

There exists a need in the art for a PGD$_2$ metabolite and assay therefore for use in research methods as well as methods useful for clinical applications. The present invention addresses and meets these needs.

SUMMARY OF THE INVENTION

The invention provides A substantially pure compound according to Formula II:

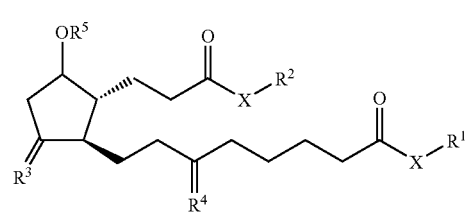

wherein:

X in each instance is independently O, NH or NR'";

R$^1$, R$^2$ and R$^5$ are independently H, alkyl, phenyl, or benzyl;

and R$^3$ and R$^4$ are independently O, NH, NR'"), NOH or NOR'";

and wherein R'" is selected from the group consisting of: halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino, acylamino, amidino, imino, oxime, sulfhydryl, alkylthio, arylthio, thiocarboxylate, sulfate, sulfonato, sulfamoyl, sulfonamido, nitro, trifluoromethyl, cyano, azido, heterocyclyl, an aromatic moiety, a heteroaromatic moiety and a fluorescent label fragment.

In a preferred embodiment, the compound is according to Formula I (herein called tetranor PDGM):

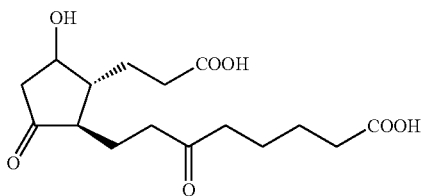

I

The invention further comprises compositions containing a compound of the invention, and an antibody the specifically binds the compound according to Formula II, and more preferably, Formula I.

A method for detecting a prostaglandin $D_2$ ($PGD_2$) metabolite in a sample is provided. The method includes the step of detecting tetranor PGDM in said sample. A method for detecting a change in $PGD_2$ in a subject is provided, comprising the steps of assessing a first level of tetranor PGDM in a biological sample obtained from the subject, and assessing a second level of tetranor PGDM in a biological sample obtained from the subject under a different condition, wherein a difference in the first level to the second level is indicative of a change in $PGD_2$ in the subject.

A method of monitoring occurrence of an acute vascular injury during a medical procedure is provided. The method comprises the steps of assessing a first level of tetranor PGDM in a biological sample obtained from the subject prior to the medical procedures and assessing a second level of tetranor PGDM in a biological sample obtained during the procedure. An acute vascular injury is indicated when the second level is increased over the first level. A method of assessing risk of acute myocardial infarction and/or late restenosis after angioplasty is also provided.

The invention further provides a method of identifying a subject who is a candidate for $PGD_2$ suppression therapy. The $PGD_2$ therapy may be DP1 antagonist therapy, DP2 antagonist therapy or PGD synthase inhibitor therapy.

A method of identifying an inhibitor of PGD synthase is provided. The method comprises measuring a first level of tetranor PGDM in a biological sample obtained from an animal that expresses PGD synthase, administering a test compound to the animal; and measuring a second level of tetranor PGDM in a biological sample obtained from the animal after administration of the test compound. A test compound that reduces the second level of tetranor PGDM compared to the first level of tetranor PGDM is identified as an inhibitor of PGD synthase.

Kits for detecting a prostaglandin $D_2$ ($PGD_2$) metabolite are also provided.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A comprises a chromatogram of $d_6$-tetranor PGDM (upper), and a chromatogram of co-eluted peaks corresponding to the endogenous compound (lower) in mouse urine. FIG. 1B comprises a chromatogram of $d_6$-tetranor PGDM (upper), and a chromatogram of co-eluted peaks in mouse urine following intra peritoneal administration of 500 μg of $PGD_2$ (lower). FIG. 1C comprises a chromatogram of $d_6$-tetranor PGDM (upper), and a chromatogram of co-eluted peaks in human urine (lower). Transitions characteristic of $d_6$-tetranor PGDM (m/z 391→342) and tetranor PGDM (m/z 385→336) are shown in the upper and lower panels, respectively, of FIGS. 1A, 1B and 1C. FIG. 1D depicts a production spectrum of $d_6$-tetranor PGDM (deuterated tetranor PGDM). The structure of derivatized $d_6$-tetranor PGDM is shown. FIG. 1E depicts a product ion spectrum of endogenous tetranor PGDM. The structure of derivatized tetranor PGDM is shown. FIG. 1F depicts a representative selected reaction monitoring chromatogram of 11β-$PGF_{2\alpha}$ in human urine. Transitions characteristic of $^{18}O_2$-11β-$PGF_{2\alpha}$ (m/z 357→197) and 11β-$PGF_{2\alpha}$ (m/z 353→193) are shown in the upper and lower panel, respectively. A peak corresponding to endogenous material co-eluting with the standard is not evident in the lower panel. FIG. 1G depicts a representative selected reaction monitoring chromatogram of 2,3-dinor-11β-$PGF_{2\alpha}$ in human urine. Transitions characteristic of $^{18}O_2$-2,3-dinor-11β-$PGF_{2\alpha}$ (m/z 329→145) and 2,3-dinor-11β-$PGF_{2\alpha}$ (m/z 325→145) are shown in the upper and lower panel, respectively.

FIG. 2A is a bar graph of the level of tetranor PGDM, 2,3-dinor-11β-$PGF_{2\alpha}$, and 11β-$PGF_{2\alpha}$ detected in human urine (normalized with respect to creatinine). FIG. 2B is a bar graph of the level of tetranor PGDM, 2,3-dinor-11β-$PGF_{2\alpha}$ and 11β-$PGF_{2\alpha}$ detected in murine urine (normalized with respect to creatinine). FIG. 2C is a bar graph of the level of tetranor PGDM detected in wild type mice, mice with knockout of lipocalin-type PGD synthase (L-PGDS$^{-/-}$) and mice with knockout of hematopoietic PGD synthase (H-PGDS$^{-/-}$). FIG. 2D depicts the level of $PGD_2$ metabolites detected in mouse urine following administration of various amounts of $PGD_2$. (■=tetranor PGDM; ▼=2,3-dinor-11β-$PGF_{2\alpha}$; ●=11β-$PGF_{2\alpha}$). FIG. 2E depicts the level of $PGD_2$ metabolites detected in mouse urine following administration intraperitoneal administration of 500 μg $PGD_2$ Data shown are the mean±SEM. (*P<0.05, P<0.01, *P<0.001).

FIG. 3A depicts data for urinary tetranor PGDM (left panel) and 2,3-dinor-11β-$PGF_{2\alpha}$ (right panel) before and after administration of a placebo or rofecoxib. FIG. 3B depicts data for urinary tetranor PGDM (left panel) and 2,3-dinor-11β-$PGF_{2\alpha}$ (right panel) before and after administration of aspirin. Data shown are the mean±SEM. (*P<0.05).

FIG. 4A is a graph of levels of tetranor PGDM in urine after LPS administration. FIG. 4B is a graph of levels of 2,3-dinor-11β-$PGF_{2\alpha}$ in urine after LPS administration. FIG. 4C is a time course of temperature in healthy volunteers before and after administration of LPS. Data shown in FIGS. 4A-4C are the mean±SEM.

(\*P<0.05, \*\*\*P<0.001). FIG. 4D depicts a correlation between log transformed urinary tetranor PGDM and 2,3-dinor-11β-PGF$_{2α}$ values.

FIG. 5A depicts a time course of urinary tetranor PGDM at various time points before (time 0) and after 400 mg or 600 mg niacin administration to two healthy volunteers. FIG. 5B depicts a time course of urinary 2,3-dinor-11β-PGF$_{2α}$ at various time points before (time 0) and after 400 mg or 600 mg niacin administration to two healthy volunteers.

DETAILED DESCRIPTION OF THE INVENTION

Figure 1A:
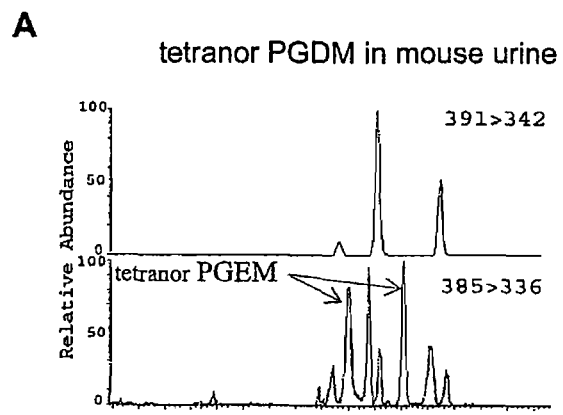
FIGS. 1A-1G are a series of representative chromatograms obtained from HPLC/MS/MS analysis of urine.

The invention arises from the discovery that 11,15-dioxo-9α-hydroxy-2,3,4,5-tetranor-prostan-1,20-dioic acid (tetranor PGDM) is a metabolite of prostaglandin D$_2$. It has further been discovered that tetranor PGDM is abundant in the urine of both humans and mice.

Consequently, the present application features a substantially purified 11,15-dioxo-9α-hydroxy-2,3,4,5-tetranor-prostan-1,20-dioic acid and derivatives thereof, compositions comprising substantially purified 11,15-dioxo-9α-hydroxy-2,3,4,5-tetranor-prostan-1,20-dioic acid, as well as methods for detecting the same in a biological specimen. The method is useful in many applications, including but not limited to, research, diagnostic and clinical.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, and nucleic acid chemistry and hybridization are those well known and commonly employed in the art.

The nomenclature used herein and the laboratory procedures used in analytical chemistry and organic syntheses described below are those well known and commonly employed in the art. Standard techniques or modifications thereof, are used for chemical syntheses and chemical analyses.

Standard techniques are used for the synthesis and manipulation of nucleic acid and peptides. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y.; Ausubel et al., 2002, Current Protocols in Molecular Biology, John Wiley & Sons, New York, N.Y.; Gerhardt et al. eds., 1994, Methods for General and Molecular Bacteriology, American Society for Microbiology, Washington, D.C.), which are provided throughout this document.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

"Instructional material," as that term is used herein, includes a publication, a recording, a diagram, or any other medium of expression which can be used to communicate the usefulness of the composition in the kit in the practice of a method of the invention. The instructional material of the kit may, for example, be affixed to a container that contains the composition of the invention or be shipped together with a container which contains the compound and/or composition. Alternatively, the instructional material may be shipped separately from the container with the intention that the recipient uses the instructional material and the composition cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"PGD$_2$" as used herein refers to prostaglandin D$_2$.

"PGD$_2$ metabolite" as used herein refers to a byproduct of PGD$_2$ metabolism in an animal, preferably in a mammal. Non-limiting examples of PGD$_2$ metabolites include 2,3-dinor-11β-PGF$_{2α}$, 11β-PGF$_{2α}$ and 11,15-dioxo-9α-hydroxy-2,3,4,5-tetranor-prostan-1,20-dioic acid.

As used herein "tetranor PGDM" refers to PDG$_2$ metabolite 11,15-dioxo-9α-hydroxy-2,3,4,5-tetranor-prostan-1,20-dioic acid.

By the term "specifically binds," as used herein with respect to an antibody, is meant an antibody which recognizes an specific antigen, but does not substantially recognize or bind other molecules in a sample. For instance, in a sample containing tetranor PGDM, an antibody that specifically binds to tetranor PGDM recognizes and binds to tetranor PGDM but does not substantially recognize or bind to other molecules in the sample.

As used herein, "PGD synthase" refers to an enzyme (E.C. 5.3.99.2) which catalyzes the isomerization of PGH$_2$ to produce PGD$_2$. There are two types of PGD synthase, a lipocalin-type and a hematopoietic type. "PGDS" is used herein as an abbreviation for PGD synthase.

As used herein, "PGD synthase inhibitor compound" or "PGD synthase inhibitor" refers to a compound which inhibits PGS synthase enzymatic activity thereby reducing $PGD_2$ biosynthesis.

As used herein, "inhibiting" an enzyme, such as PGD synthase, should be construed to include: inhibiting the enzymatic activity of the enzyme, inhibiting the transcription of the enzyme gene, and inhibiting the translation of the enzyme mRNA. Inhibiting the enzymatic activity of an enzyme includes reducing the half-life of the enzyme, for instance, by increasing degradation of either the enzyme and/or the mRNA for the enzyme. "Inhibiting" as used herein refers to a detectable reduction in an activity or process resulting from administration of a drug compared to the activity or process prior to the administration of the drug. Detectable reduction encompasses both indirect and direct detection of such reduction.

A "COX enzyme" is used herein to refer to an enzyme (EC 1.14.99.1) having cyclooxygenase activity. These enzymes catalyze the formation of prostaglandins and thromboxane from arachidonic acid by means of their cyclooxygenase and peroxidase activities. Alternative names include: fatty acid cyclooxygenase, prostaglandin-endoperoxide synthase, prostaglandin-endoperoxide synthetase, prostaglandin synthase, prostaglandin synthetase, PG synthetase, (PG)H synthase, and prostaglandin G/H synthase. There are two isoforms of cyclooxygenase, referred to as COX-1 and COX-2. Alternative names for these enzymes include PGHS-1 and PGHS-2, respectively.

"$PGE_2$" as used herein refers to prostaglandin $E_2$.

"$PGE_2$ metabolite" as used herein refers to a byproduct of $PGE_2$ metabolism in an animal, preferably in a mammal. As used herein, "tetranor PGEM" refers to the $PGE_2$ metabolite 9,15-dioxo-11α-hydroxy-2,3,4,5-tetranor-prostan-1,20-dioic acid.

The term "substantially pure" describes a compound, e.g., a protein or polypeptide, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides, by column chromatography, gel electrophoresis or HPLC analysis. A compound, e.g., a protein, is also substantially purified when it is essentially free of naturally associated components or when it is separated from the native contaminants which accompany it in its natural state.

As used herein, "therapeutically effective amount" refers to a nontoxic but sufficient amount of an agent to provide the desired biological result. That result can be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in an inducible manner.

A "constitutive promoter" is a promoter which drives expression of a gene to which it is operably linked, in a constant manner in a cell. By way of example, promoters which drive expression of cellular housekeeping genes are considered to be constitutive promoters.

It is understood that any and all whole or partial integers between any ranges set forth herein are included herein.

DESCRIPTION OF THE INVENTION

The invention provides a substantially pure compound having the structure shown in Formula I

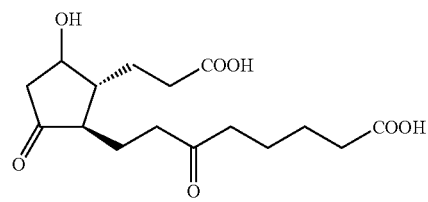

that is named 11,15-dioxo-9α-hydroxy-2,3,4,5-tetranor-prostan-1,20-dioic acid (tetranor PGDM). The compound has been discovered to be a metabolite of $PGD_2$ that is abundant in urine of both humans and mice. This metabolite is the first $PGD_2$ metabolite identified in mice. The property of being abundant in urine is advantageous in that it permits non-invasive analytic approaches. In addition, it has been discovered that the compound is a sensitive and specific molecular marker of the level of $PGD_2$ in a mammal. Accordingly, the compound is useful in research applications, as well as for medical applications. The invention further provides a composition comprising the compound, and an antibody that specifically recognizes the compound. The antibody may be polyclonal or monoclonal.

The invention further embraces derivatives of the compound. Non-limiting examples of tetranor PGDM derivatives include stable-isotope-labeled, e.g. deuterium (2H) or oxygen-18 ($^{18}O$), tetranor PGDM, and radiolabeled tetranor PGDM. The tetranor PGDM molecule may be radiolabeled with isotopes such as, but not limited to, $^{14}C$ or $^3H$, and the radiolabeled PGDM molecule may contain one or more such radioactive isotopes. Such derivatives may be prepared using common methods known to those individuals skilled in the art.

A tetranor PGDM derivative is depicted in Formula II,

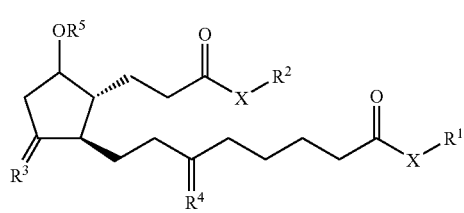

wherein X in each instance is independently O, NH or NR'''; $R^1$, $R^2$ and $R^5$ are independently H, alkyl, phenyl, or benzyl; and $R^3$ and $R^4$ are independently O, NH, NR''', NOH or NOR'''. Depending on the choice of $R^1$, $R^2$, $R^3$, $R^4$ or $R^5$, the derivative depicted in Formula II may represent a fluorescently-labeled derivative.

The term "alkyl" refers to saturated aliphatic groups, including straight-chain alkyl groups, branched-chain alkyl groups, cycloalkyl, heterocyclyl, cycloalkyl (alicyclic) groups, alkyl substituted cycloalkyl groups, and cycloalkyl substituted alkyl groups. In preferred embodiments, a straight chain or branched chain alkyl has 8 or fewer carbon atoms in its backbone (e.g., $C_1$-$C_8$ for straight chain, $C_3$-$C_8$ for branched chain). In another preferred embodiment, cycloalkyls have from 3-8 carbon atoms in their ring structure. Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen atom on one or more carbon atoms of the hydrocarbon backbone, which allow the molecule to perform its intended function.

Examples of substituents of the invention, which are not intended to be limiting, include moieties selected from straight or branched $C_1$-$C_5$ alkyl, $C_3$-$C_6$ cycloalkyl, $C_1$-$C_3$ alkoxy, $C_1$-$C_3$ thioalkyl, $C_2$-$C_6$ alkenyl, heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R'''$ (e.g., $—NH_2$), $(CR'R'')_{0-3}$ CN (e.g., —CN), halogen (e.g., —F, —Cl, —Br, or —I), $CF_3$, $(CR'R'')_{0-3}CONR'R'''$, $(CR'R'')_{0-3}$ $(CNH)NR'R'''$, $(CR'R'')_{0-3}$ $S(O)_{1-2}NR'R'''$, $(CR'R'')_{0-3}CHO$, $(CR'R'')_{0-3}O(CR'R'')_{0-3}H$, $(CR'R'')_{0-3}S(O)_{0-4}R'$ (e.g., $—SO_3H$, $—OSO_3H$), $(CR'R'')_{0-3}$ $O(CR'R'')_{0-3}H$ (e.g., $—CH_2OCH_3$ and $—OCH_3$), $(CR'R'')_{0-3}$ $S(CR'R'')_{0-3}H$ (e.g., —SH and $—SCH_3$), $(CR'R'')_{0-3}OH$ (e.g., —OH), $(CR'R'')_{0-3}COR'$, $(CR'R'')_{0-3}$(substituted or unsubstituted phenyl), $(CR'R'')_{0-3}$(cycloalkyl), $(CR'R'')_{0-3}CO_2R'''$ (e.g., $—CO_2H$), or $(CR'R'')_{0-3}OR'''$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, aryl group, and R''' is hydrogen, a $C_1$-$C_5$ alkyl, $C_2$-$C_5$ alkenyl, $C_2$-$C_5$ alkynyl, aryl group, or a fluorescent label fragment. The fluorescent labels may include any molecule known in the art that either imparts inherent fluorescent behavior to a molecule to which it is attached or changes fluorescent behavior upon binding to a target or reacting with a substrate. Examples of fluorescent label fragments include, but are not limited to, 2-(6-hydroxy-3-oxo-3H-xanthen-9-yl) benzenecarbonyl, 2-(2,4,5,7-tetrabromo-6-hydroxy-3-oxo-3H-xanthen-9-yl)benzenecarbonyl and 2-(2,4,5,7-tetraiodo-6-hydroxy-3-oxo-3H-xanthen-9-yl)benzenecarbonyl.

R', R" and R''' can include, but are not limited to, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, acylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfate, sulfonato, sulfamoyl, sulfonamido, nitro, trifluoromethyl, cyano, azido, heterocyclyl, or an aromatic or heteroaromatic moiety. R''' may also include fluorescent label fragments, such as, but not limited to, 2-(6-hydroxy-3-oxo-3H-xanthen-9-yl)benzenecarbonyl, 2-(2,4,5,7-tetrabromo-6-hydroxy-3-oxo-3H-xanthen-9-yl)benzenecarbonyl and 2-(2,4,5,7-tetraiodo-6-hydroxy-3-oxo-3H-xanthen-9-yl) benzenecarbonyl. It will be understood by those skilled in the art that the moieties substituted on the hydrocarbon chain can themselves be substituted, if appropriate.

Figure 1B:
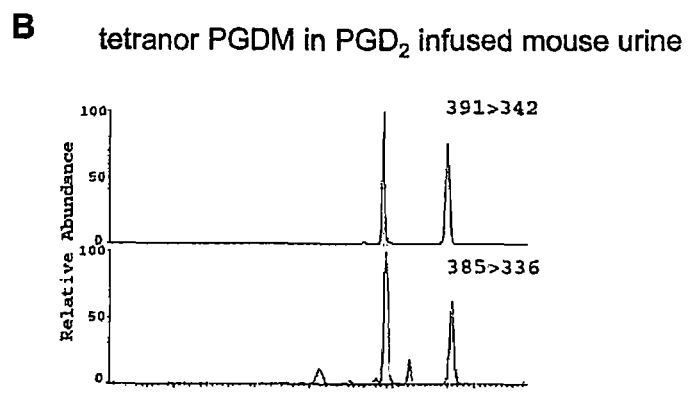
Figure 1C:
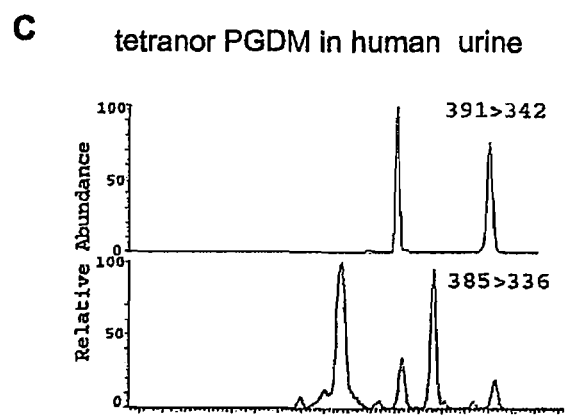
Figure 1D:
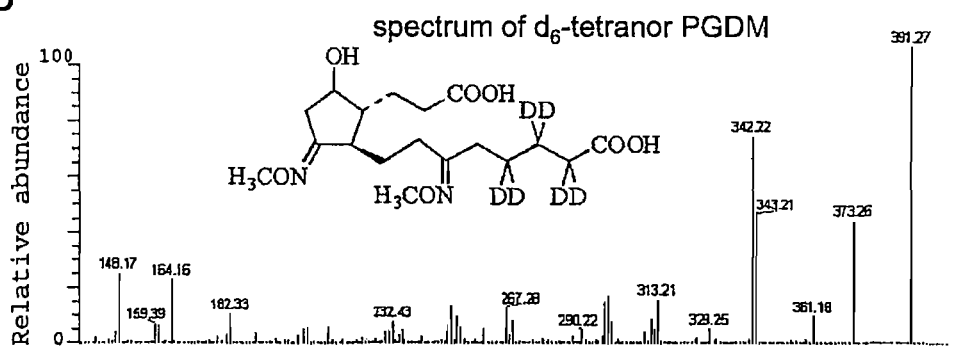
Figure 1E:
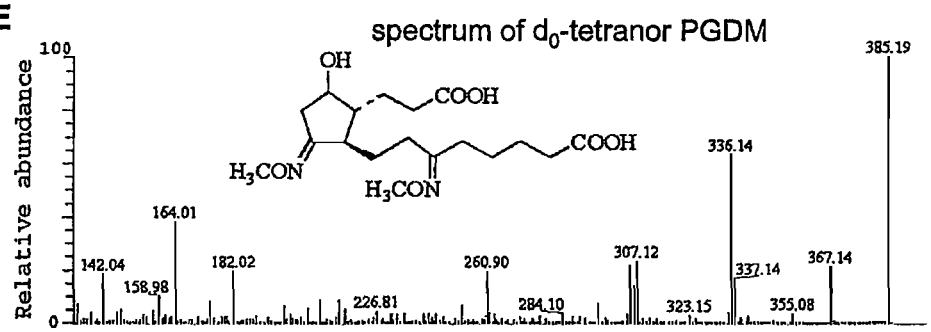

An exemplary derivative is depicted in FIG. 1E, wherein $R^3$ and $R^4$ are NOR''' and wherein R''' is a methyl group. Thus in one embodiment, $R^3$ and $R^4$ are identical. The skilled artisan will recognize that other derivatives exist and these are encompassed by the invention.

The compound of the invention may be obtained by purification from a biological sample or may be synthesized chemically using standard techniques known in the art.

"Biological sample" as used herein refers to a tissue sample or body fluid. Exemplary body fluids include, but are not limited to, blood, blood components (e.g., serum, plasma), urine, and cerebrospinal fluid (CSF). Preferred biological sources of tetranor PGDM include urine, more preferably, mouse or human urine, and more preferably still, human urine.

The biological sample may be obtained from any animal that has endogenous $PGD_2$, or is recombinantly engineered to biosynthesize $PGD_2$. Non-limiting examples of animals from which a biological sample may be obtained are mammals, such as humans, non-human primates, cattle, horses, dogs, sheep, goats, mice, rats and pigs. Preferably, the animal is a human.

The compound may be purified from the biological sample using any method known in the art. Useful isolation methods include, by way of example, and not by limitation, purification methods such as solvent extractions, solid phase extractions, chromatographic methods, thin-layer chromatography methods, centrifugation and sedimentation methods, among others. Chromatographic methods include affinity chromatography using an antibody that specifically binds to tetranor PGDM and high pressure liquid chromatography (HPLC). An exemplary purification method using liquid chromatography/tandem mass spectrometry (LC/MS/MS) is described in the Examples.

Another preferred method of isolating tetranor PGDM is as follows. Briefly, the tetranor PGDM is isolated by first, in the case of a tissue sample, homogenizing the tissue sample. In the case of a body fluid sample, no homogenization step is necessary. Total lipids are then extracted from the sample using ice-cold Folch solution, chloroform/methanol (2:1, v/v). The solution is then centrifuged briefly, and the organic phase, which contains the extracted lipids, is dried under nitrogen.

Assessing the level of tetranor PGDM may be achieved using techniques and methods known to the skilled artisan for assessing, measuring, assaying or quantifying a prostaglandin molecule may be used. Such methods are described, for example, in Lawson et al. (1999, J. Biol. Chem., 374(35) 24441-24444). These methods include, by way of example, and not by limitation, quantitative and semi-quantitative methods such as chromatographic methods including thin layer chromatography, low, medium, and high pressure liquid chromatography methods, mass spectrometry methods, gas chromatography methods, gas chromatography/mass spectrometry methods, and immunological methods. Preferably, the assay is a quantitative assay. The level of the tetranor PGDM is quantified based on the assay results using, for example, peak area or peak height ratios. An example of assessing the level of tetranor PGDM in a biological sample using LC/MS/MS is described herein in the Examples.

Another method for assaying the tetranor PGDM isolated using the above-described total lipid extraction method includes the following steps: the sample which contains the tetranor PGDM is spiked with a known amount of a synthetic homologous internal standard, such as deuterated tetranor PGDM or a radio-labeled synthetic tetranor PGDM molecule. The samples are then subjected to solid phase extraction, derivatized, and purified using thin layer chromatography. After thin layer chromatography, each sample is analyzed for tetranor PGDM content using gas chromatography-mass spectrometry, and quantitation is performed using peak area or peak height ratios.

A method of detecting a $PGD_2$ metabolite is thus provided by the invention. The method comprises detecting tetranor PGDM in the sample. Any detection method known in the art may be used. Non-limiting examples of detecting methods include LC/MS/MS and immunoassays. Such a method is useful in many different applications. Tetranor PGDM is a biomarker for any $PGD_2$-induced bioactivity, such as activation of mast cells or mastocytosis. Accordingly, mast cell activation can be monitored or assessed by detecting the level of tetranor PGDM in a biological sample, preferably urine. Furthermore, as discovered herein, inhibition of COX-1 markedly decreases the level of tetranor PGDM in urine. Thus, measuring the level of urinary PGDM can be used in a method to identify candidate COX-1 inhibitors. In addition, it has been discovered that both lipocalin-type and hematopoietic PGD synthases directly influence the level of urinary tetranor PGDM. Accordingly, measuring the level of urinary tetranor PGDM can be used in a method to identify candidate PGD synthase inhibitors.

Inhibitors of an enzymatic activity can be identified by screening test compounds using organisms, such as mice, that express COX-1 or a PGD synthase. The organism may express an endogenous PGD synthase or COX-1 or a heterologous PGS synthase or COX-1. In one embodiment, expression of the endogenous enzyme is reduced or eliminated by standard known to the skilled artisan, including but not limited to gene knock out, gene knock down and RNAi, and a heterologous gene is introduced into a cell in the organism. The organism may be a transgenic animal.

A COX-1 or PGD synthase may be expressed from a heterologous gene introduced into the animal by recombinant methods. The introduced heterologous nucleic acid may be present transiently, or may be present stably in a cell, for instance due to insertion into a cell's chromosomal material. Expression of the heterologous gene may be constitutive or inducible.

The skilled artisan is familiar with the many methods of introducing heterologous nucleic acid into a cell of an organism or in the preparation of transgenic organism, as well as the sequence elements necessary for transcription and translation of a coding sequence. See, for instance, Sambrook et al. (2001, Molecular Cloning: A Laboratory Manual, Cold Spring Harbor Laboratory Press, Cold Spring Harbor, N.Y.), in Ausubel et al. (eds., 1997, Current Protocols in Molecular Biology, John Wiley & Sons, New York), and in Gerhardt et al. (eds., 1994, Methods for General and Molecular Bacteriology, American Society for Microbiology, Washington, D.C.). In a preferred embodiment of the method, the COX-1 and/or PGD synthase, or variant thereof, is from the same organism that is the intended recipient of treatment with the so-identified COX-1 or PGS synthase inhibitor.

COX-1 and PGD synthase have been obtained and sequenced in several organisms, and any one can be used in the instant invention. PGD synthase coding sequences useful in the instant invention include, but are not limited to: human L-PGDS (mRNA, NCBI GenBank® Accession number NM_000954) and H-PGDS (mRNA, NCBI GenBank® Accession number NM_014485). Furthermore, any sequence encoding a variant COX-1 or PGD synthase can be used, provided the COX-1 or PGD synthase variant protein retains the activity of producing $PGD_2$. Methods for assessing $PGD_2$ production are discussed elsewhere herein.

The heterologous PGD synthase or COX-1 coding sequence may be operably linked to other nucleic acid sequences. Nonlimiting examples of other nucleic acid sequences are inducible promoters and other coding sequences, such as protein tags. By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region. Inducible promoters are useful for controlled overexpression of the heterologous sequence. Protein tags, such as affinity tags or epitopes, are useful, for instance, in simplifying purification of the fusion protein. Sequences of inducible promoters and protein tags are well known in the art to the skilled artisan.

To identify a test compound as an inhibitor of COX-1, COX-2 and/or PGD synthase, the $PGD_2$ level may be assessed indirectly in a biological sample from the organism after exposure to a test compound by assessing tetranor PGDM in the biological sample. The level is then compared to a tetranor PGDM level in a biological sample in the absence of the test compound. Preferably the biological sample is the same for both the first and second measurements. A test compound that reduces tetranor PGDM is identified as an inhibitor of COX-1, COX-2 and/or PGD synthase. In a preferred embodiment, the biological sample is urine. The skilled artisan is knowledgeable about the appropriate control experiments necessary to confirm that a inhibitor is acting directly on the enzyme of interest. For instance, test compounds identified as a COX or PGS synthase inhibitor may be tested using a purified enzyme in an in vitro assay, or a cell-based assay using a cell that expresses the enzyme of interest, for inhibition of the production of PGD2 in the presence of the test compound.

Test compounds for use in the screening methods can be small molecules, nucleic acids, peptides, peptidomimetics and other drugs. The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam, 1997, Anticancer Drug Des. 12:145). Test compounds may also be designed based on the known enzyme substrates. Thus, test compounds may comprise analogs of arachidonic acid or $PGH_2$. Inhibitors of mPGES-1 activity identified by the inventive method may be useful directly in therapeutic applications, and may also serve as lead drugs in the development of further therapeutics.

As demonstrated elsewhere herein, the amount of urinary tetranor PGDM is expected to be proportional to the amount of $PGD_2$ present in a subject, therefore, measuring tetranor PGDM in the urine of the subject can be used to assess the level of $PGD_2$ indirectly. In one application, a change in $PGD_2$ in a subject is detected. In this method, a first level of tetranor PGDM is measured in a biological sample obtained from the subject. The first level is then compared to a second level of tetranor PGDM measured in a biological sample from the subject under a different condition. A difference in the two levels is proportional to a change in $PGD_2$. The different condition may be, for instance, a different point in time, the occurrence of a medical procedure, the presence of a therapeutic agent or a change in clinical status (e.g., diagnosis of mastocytosis).

As demonstrated herein, transient elevation of $PGD_2$ may be a protective reaction to acute vascular injury/insult, such as that which occurs during angioplasty. Accordingly, monitoring tetranor PGDM during angioplasty may serve to monitor the occurrence and/or magnitude of vascular injury. A method of monitoring occurrence and/or magnitude of an acute vascular injury during a medical procedure known or likely to induce vascular injury, such a angioplasty or other cardiac catheterization procedure, is therefore provided. The method comprises assessing a first level of tetranor PGDM in a biological sample obtained from the patient prior to the medical procedure, and assessing a second level of tetranor PGDM in a biological sample obtained from the patient during the medical procedure, wherein if the second level is increased compared to the first level, it is indicative of the occurrence of an acute vascular injury. The extent of increase is expected to correlate with the magnitude of vascular injury. The skilled artisan is familiar with determining what degree of elevation correlates with the occurrence of an acute vascular injury, for instance, by comparison to a reference level indicative of vascular injury. Optionally the reference level is stratified with respect to age, gender, medical history, and/or other parameters.

The occurrence and/or magnitude of vascular injury might further be predictive of risk of myocardial infarction and/or late restenosis. It is also shown herein that aspirin therapy suppresses the protective release of $PGD_2$. The aspirin suppression observed during angioplasty may contribute to an increased risk of acute myocardial infarction and/or late restenosis, adverse post-angioplasty events. "Late restenosis" refers to restenosis occurring at least 6 to 9 months or more preferably, 12 months after angioplasty. Suppressed levels of $PGD_2$ prior to angioplasty and/or insufficient elevation of $PGD_2$ during angioplasty therefore may indicate a patient at an increased risk of acute myocardial infarction and/or last restenosis. Thus, the invention contemplates a method of assessing risk of acute myocardial infarction and/or late restenosis after angioplasty or other cardiac procedure (such as cardiac catherization) comprising assessing a first level of tetranor PGDM in a biological sample obtained from the patient prior to the cardiac procedure, assessing a second level of tetranor PGDM in a biological sample obtained from the patient during the cardiac procedure, wherein an insufficient increase difference from said first level to said second level is indicative of an increased risk of acute myocardial infarction in said subject, relative to a subject having a sufficient transient increase in $PGD_2$. Identifying what constitutes sufficient increase and insufficient increase with regard to risk of acute myocardial infarction is readily accomplished by the skilled artisan using conventional methods in the art. Increase may refer to an absolute increase or to a relative value, for instance a ratio of the before and during levels or by comparison to a reference level for one or more individuals whose risk of acute myocardial infarction is known. Measuring tetranor PGDM may also be useful in diagnosing acute coronary syndrome.

Measuring urinary tetranor PGDM may also be used to identify a patient who has a chronically elevated $PGD_2$ level and are therefore candidates for prostaglandin $D_2$ suppression therapy, such as DP1 or DP2 antagonist therapy or PGD synthase inhibitor therapy. The method comprises assessing a level of tetranor PGDM in a biological sample from the patient and comparing the level to a reference level that is indicative of normal level of $PGD_2$. A normal level of $PGD_2$ may differ based on gender, age, medical history and/or other parameters; the skilled artisan is familiar with determining reference levels. Patients who are candidates for DP1 antagonist therapy, for instance, include those who are candidates for niacin therapy. Niacin is a hypolipedemic drug that in some patients causes the unpleasant side effect of facial flushing. The facial flushing is believed to be caused by $PGD_2$ binding to DP1. Thus, antagonizing $PGD_2$ binding to DP1 is expected to reduce the flushing side effect. The level of urinary tetranor PGDM could be measured in a patient before and after administration of niacin to ascertain if niacin-induced facial flushing is accompanied by an increase in urinary PGDM, which corresponds to an increase in $PGD_2$. A patient whose urinary PGDM does increase when administered niacin is identified as candidate likely to respond to therapy using a DP1 antagonist or PGD synthase inhibitor. In another application, measuring tetranor PGDM in urine can be used to assess the efficacy of a PGD synthase inhibitor. Comparing urinary tetranor PGDM measured before and after dosing with a PGD synthase inhibitor will indicate whether the inhibitor sufficiently lowers the level of $PGD_2$ to an appropriate level. The skilled artisan can individualize PGD synthase inhibitor therapy for an individual by assessing the effects of a particular dosing regimen in order to optimize the balance of therapeutic benefit and any potential adverse effects due to excessive suppression of $PDG_2$.

Similarly, the skilled artisan can individualize DP1 antagonism therapy for an individual by assessing the effects of a particular dosing regimen in order to optimize the balance of therapeutic benefit and any potential adverse effects due to excessive inhibition of $PDG_2$ activity. Accordingly, a method for assessing a dosage of a DP1 antagonist in an individual who is undergoing DP1 antagonist therapy or is a candidate for such therapy includes measuring a first level of tetranor PGDM in a biological sample obtained from the individual prior to administering the dosage of a DP1 antagonist, measuring a second level of tetranor PGDM in a biological sample obtained from the individual after administering the dosage of a DP1 antagonist, wherein when the second level of tetranor PGDM is sufficiently changed compared to the first level of tetranor PGDM, the dosage is identified as likely providing therapeutic benefit. The skilled artisan is readily able to determine what change qualifies as a sufficient change without undue experimentation. For instance, databases of average ranges of $PGD_2$ levels under different circumstances may be generated and used as a point of comparison. Such methods of assessing a dosage of a therapeutic agent will allow the skilled practitioner to titrate the dose for a particular individual to identify a therapeutically effective amount, as well as minimizing any suspected adverse effect with the dose.

For this and other quantitative assays, urine is collected in sterile containers, preferably 30 minutes after voiding. Alternatively, urine is collected as a time integrated sample. For instance, after voiding, urine is collected for a time period, for instance 2, 4 or 6 hours. At the end of the time period, the bladder is voided again and the sample collection is then complete. If the urine sample is not analyzed immediately, the sample is stored in such a way as to prevent or reduce breakdown of the component(s) to be measured in the urine. One method of storage to prevent or reduce breakdown is to freeze the sample on dry ice immediately after collection and store the frozen sample at $-70°$ C.

Tetranor PGDM levels in urine are generally normalized to another urine component. Typically, the other urine component is creatinine. Creatinine is measured is preferably measured using an automated colorimetric assay (Sigma-Aldrich Co., St Louis, Mo.).

Assessing the level of tetranor PGDM in a biological sample is preferably accomplished using LC/MS/MS as described elsewhere herein. However, the skilled artisan may use any quantitative method of the level of a prostaglandin. For instance, immunodetection using an antibody that specifically binds to tetranor PGDM may be used. Methods for the preparation and purification of antibodies are known in the art, and are described, for example, in Harlow et al., 1988, Antibodies: A Laboratory Manual, Cold Spring Harbor, N.Y. Immunoassays useful in the present invention include for example, immunohistochemistry assays, immunocytochemistry assays, ELISA, capture ELISA, sandwich assays, enzyme immunoassay, radioimmunoassay, fluorescent immunoassay, and the like, all of which are known to those of skill in the art. See e.g. Harlow et al., 1988, supra; Harlow et al., 1999, Using Antibodies: A Laboratory Manual, Cold Spring Harbor Laboratory Press, NY.

A kit is envisaged for every method disclosed herein. Thus, the invention also includes a kit for detecting a $PGD_2$ metabolite in a sample and includes an instructional material describing how to use the kit contents to detect a $PGD_2$ metabolite. In one embodiment, the kit comprises a synthetic tetranor PGDM standard, useful in LC/MS/MS methods for detecting tetranor PGDM. Optionally, the kit comprises a container for a biological sample. The kit optionally further comprises a solution useful in the extraction of tetranor PGDM from a biological sample. Preferably, the solution is an ethanol solution.

In another embodiment, the kit comprises an antibody that specifically binds to tetranor PGDM. Optionally, the kit further comprise a sample of substantially purified tetranor PGDM to be used as a positive control. The antibody can be any type of antibody known in the art. The kit can, optionally, include a secondary antibody directed against the antibody specific for tetranor PGDM.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The materials and methods used in the experiments presented in the Experimental Examples below are now described.

Standards: Synthetic PGDM comprising 6 deuterium in place of 6 hydrogen atoms ($d_6$-tetranor PGDM) was synthesized on request by Cayman Chemicals (Ann Arbor, Mich.). Authentic 2,3-dinor-11β-$PGF_{2\alpha}$, 9α,11β-$PGF_{2\alpha}$, $PGD_2$ and 9α,11β-$PGF_{2\alpha}$ were purchased from the same source for use as standards. $H_2{}^{18}O$ was purchased from Cambridge Isotope Laboratories (Andover, Mass.). HPLC-grade water was utilized (Milli-Q water purification system, Millipore) in the preparation of all aqueous solutions and mobile phases. HPLC-grade acetonitrile and ethyl acetate was purchased from J. T. Baker. Reagent-grade acetic acid was purchased from Fisher. HPLC-grade ammonium hydroxide was purchased from Mallinckrodt. ${}^{18}O_2$-2,3-dinor-11β-$PGF_{2\alpha}$, and ${}^{18}O_2$-11β-$PGF_{2\alpha}$ were prepared as previously described (Pickett et al., 1981, Anal Biochem. 111: 115-121).

Urine analysis: ${}^{18}O_2$-2,3-dinor-11β-$PGF_{2\alpha}$, and ${}^{18}O^2$-11β-$PGF_{2\alpha}$ were added to 1 milliliter (ml) of human urine or 100 ml of mouse urine and were allowed to equilibrate for 15 minutes. The pH was then adjusted with formic acid to about 3.0. The samples were purified by solid phase extraction (SPE) using StrataX cartridges (Phenomenex, Torrance, Calif.). The SPE cartridge was conditioned with 1 ml of acetonitrile and then equilibrated with 1 ml of water. The sample was applied to the cartridge, which was then sequentially washed with 1 ml 5% acetonitrile in water and dried with vacuum for 15 min. The analyte and internal standards were eluted from the cartridge using 1 ml of 5% acetonitrile in ethyl acetate. The eluate was collected and dried under a gentle stream of nitrogen. The resulting residue was then reconstituted with 100 μl of 5% acetonitrile in water and was filtered by centrifugation. The 0.2-micrometer (μm) Nylon microspin filters were purchased from Alltech Associates.

High Performance Liquid Chromatography: The HPLC included two high pressure pumps (Shimadzu, Torrance Calif.) and a Luna C18 (2) 3 m 150*2.00 mm HPLC column (Phenomenex, Torrance, Calif.). The mobile phase consisted of water (solvent A) and acetonitrile:methanol (95:5, solvent B), both with 0.005% acetic acid adjusted to pH 5.7 with ammonium hydroxide. The flow rate was controlled at 200 microliter per minute (μl/min). The separation was carried out with variant linear solvent gradient programs.

Mass Spectrometry: A Thermo Finnigan TLSQ Quantum Ultra tandem instrument (Thermo Scientific, Waltham, Mass.) equipped with a coaxial electrospray source and triple quadrupole analyzer was used in these studies. The ESI source used nitrogen for both sheath and auxiliary gas and was set at 70 and 5 (arbitrary units), respectively. The mass spectrometer was operated in the negative ion mode with a capillary temperature of 350° C. and a spray voltage of 2.0 kV. The source collision-induced dissociation (SCID) was set to 10 eV. The analyzers were set in the selected reaction monitoring (SRM) mode for the analysis of urinary $PGD_2$ metabolites. The transitions m/z 385→336 for the endogenous material and the m/z 391→342 for the deuterated internal standard were monitored for tetranor PGD-M. The collision gas was Argon (1.5 mTorr) and collision energy (CE) was 15 eV. The transitions for endogenous 2,3-dinor-11β-$PGF_{2\alpha}$ and ${}^{18}O_2$-2,3-dinor-11β-$PGF_{2\alpha}$, were m/z 325→145 and m/z 329→145 with CE 13 eV, respectively. They were m/z 353→4193 and m/z 357→197 for 9α,11β-$PGF_{2\alpha}$ and ${}^{18}O_2$-9α,11β-$PGF_{2\alpha}$ with CE 24 eV.

Product ion scan mode was used for spectral analysis of tetranor PGDM. Precursor ions (m/z 385 and 391 for endogenous tetranor PGDM and the $d_6$-tetranor PGDM internal standard, respectively) were collisionally activated at 15 eV under 1.5 mT argon gas producing the CID spectra.

Studies in mice: All studies were performed following protocol review and approval by the Institutional Animal Care and Use Committee (IAUCC) of the University of Pennsylvania. (i) Infusion studies: vehicle or $PGD_2$ [20, 150 or 500 μg] was infused i.p. into twelve-week-old male C57/BL6 mice (n=5 per group). Urine was collected for 24 hours in metabolic cages for analysis of $PGD_2$ metabolites. (ii) PGDS knockouts: Urine was collected for 24 hours from three- to four-month-old male wild type mice, L-PGDS knockout mice (kindly provided by Dr. Yoshihiro Urade, Osaka, Japan) and H-PGDS knockout mice (kindly provided by Dr. Yoshihide Kanaoka, Boston, Mass.), all on a C57/BL6 background (n=15 for WT and LPGDS knockouts and n=10 for H-PGDS knockouts).

Clinical Studies: Four clinical studies were performed. The study protocols were approved by the Institutional Review Board of the University of Pennsylvania and by the Advisory Council of the Clinical and Translational Research Center (CTRC) of the University of Pennsylvania. All volunteers were apparently healthy on physical examination, were non-smokers and refrained from all medications for 2 weeks before and then during the course of the studies. Volunteers with a history of coagulation disorders, a bleeding tendency, drug allergy, or gastrointestinal disorders were excluded from participation in the studies.

In the first study, 12 volunteers (6 male and 6 female) received a bolus injection of single dose 3 nanogram per kilogram body weight (ng/kg) of bacterial lipopolysacharide (LPS) under controlled conditions as previously described (McAdam et al., 2000, J Clin Invest 105: 1473-1482). Subjects were admitted to the CTRC the evening before the study, and an intravenous infusion of saline was commenced. The study involved a 60-hour inpatient stay in the Clinical and Translational Research Center of the University of Pennsylvania (www(dot)itmat(dot)upenn(dot)edu) comprising an overnight acclimatization phase, a 24-hour saline administration control phase, and a 24-hour post-LPS study phase. Urinary $PGD_2$ metabolites were assessed in urines collected at the following time intervals before (−24 to −18, −18 to −12, −12 to −6, −6 to 0 hrs) and after (0 to 2, 2 to 4, 4 to 6, 6 to 8, 8 to 10, 10 to 12, 12 to 18 and 18 to 24 hrs) LPS administration. Data are plotted at the mid point of each corresponding urine collection. Body temperature was recorded at the following time points before (−4 and −2 hrs) and after (0, 3, 4, 6, 8, 10, 12, 14, and 16 hrs) LPS administration.

In a second study, niacin (dose was 400 mg or 600 mg) was administered to two healthy male volunteers. Urinary $PGD_2$ metabolites were assessed in spot urines collected at the following time points before (time 0) and after (1, 2, 3, 4, 5, 6 hours) niacin administration.

In a third study, 18 healthy volunteers (9 male and 9 female) received, in random order, a single dose of placebo or rofecoxib (25 mg) under double-blind conditions, separated by washout periods of at least 2 weeks. Urinary $PGD_2$ metabolites were assessed at 0 and 4 hours in spot urine samples that were collected 30 minutes after voiding.

In a fourth study, a single dose of aspirin (325 mg) was administered to healthy volunteers (n=18; 9 males and 9 females). Urinary $PGD_2$ metabolites were assessed at time 0 in spot urines and 0-4 hours in urine collected from 0-4 hrs after dosing.

Data Analysis: Data are expressed after correction for urinary creatinine (Cr) concentrations and are reported as nanograms per milligram creatinine. Results are expressed as mean+/−SEM. Statistical comparisons were performed initially using a two-way ANOVA, with subsequent two-tailed comparisons as appropriate.

The results of the experiments are now described.

Experimental Example 1

Discovery of Tetranor PGDM

While measuring 9,15-dioxo-11α-hydroxy-2,3,4,5-tetra-nor-prostan-1,20-dioic acid (tetranor PGEM), the major urinary PGE metabolite in mouse urine (Cheng et al., 2006, J Clin Invest. 116: 1391-1399), four major peaks, apparently tetranor-PGEM isomers, were observed in the mass chromatogram (FIG. 1A, lower panel). Because $PGD_2$ and $PGE_2$ are themselves structural isomers (Hamberg et al. 1976, Biochim Biophys Acta 431: 189-83), it was hypothesized that some of these peaks might originate from $PGD_2$. To test this hypothesis, $PGD_2$ was infused into mice, which resulted in a dramatic increased in two of these four peaks (FIG. 1B, lower panel), suggesting that they corresponded to the analogous D-ring tetranor metabolites. Authentic $d_6$-tetranor PGDM added to mouse urine coeluted with the peaks corresponding to the presumptive endogenous material (FIGS. 1A and 1B).

Mass spectral analysis of human urine also revealed the existence of tetranor PGDM (11,15-dioxo-9α-hydroxy-2,3,4,5-tetranor-prostan-1,20-dioic acid), which differed from mouse only in its abundance relative to tetranor PGEM (FIG. 1C). Collision induced dissociation (CID) of the $d_6$-tetranor PGDM at m/z 391 gave rise to a series of major fragment ions with m/z values of 373, 342, 313, 267, 182, 164, 142 and a base peak of 391 (FIG. 1D), which was virtually identical to the mass spectrum obtained from endogenous tetranor PGDM m/z values of 367, 336, 307, 261, 182, 164, 142 and a base peak of 385 (FIG. 1E). The differences in m/z values between these two groups were either 0 or 6 mass units, reflecting fragments with or without deuterium, again consistent with the original hypothesis. The major fragment ions m/z 391→342 and m/z 385→636 are the same as those for tetranor PGEM, facilitating an integrated approach to lipidornic analysis (Song et al., 2007, (in press) Methods in Enz. Vol. 433).

Experimental Example 2

Figure 1F:
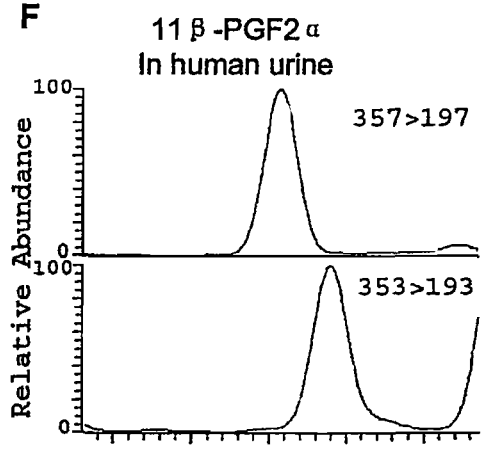
Figure 1G:
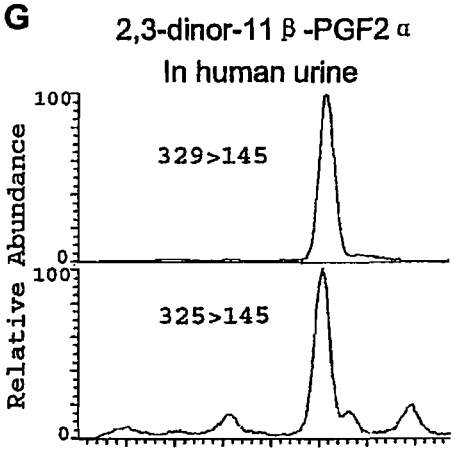

HPLC/MS/MS Analysis of Urinary
2,3-dinor-11β-$PGF_{2\alpha}$ and 11β-$PGF_{2\alpha}$ $^{18}O_2$-labeled standards of 2,3-dinor-11β-$PGF_{2\alpha}$ and 11β-$PGF_{2\alpha}$ were synthesized and utilized in quantitative analyses in urine. A representative selected reaction monitoring chromatogram of 11β-$PGF_{2\alpha}$, in human urine is shown in FIG. 1F. Transitions characteristic of $^{18}O_2$-11β-$PGF_{2\alpha}$ (m/z 357→197) and 11β-$PGF_{2\alpha}$ (m/z 353→193) are shown in the upper and lower panel, respectively. A detectable endogenous chromatographic peak that co-eluted with spike was absent from most human urine samples. Some peaks eluted close to, but not coincident with, the retention time of the standard added to the urine at the start of the procedure. These peaks were further confirmed to be distinct from endogenous 11β-$PGF_{2\alpha}$, by addition of synthetic exogenous standards at the time of analysis. It was surmised that these peaks represent F2-isoprostanes, which would have the potential to cross react with 11β-$PGF_{2\alpha}$ in an immunoassay and also may not have separated from endogenous 11β-$PGF_{2\alpha}$, under the elution conditions utilized in a GC/MS assay (O'Sullivan et al., 1999, Prostaglandins and Other Lipid Mediators, 57: 149-165). While 2,3-dinor-11β-$PGF_{2\alpha}$ was readily detectable in human urine, it required a very long HPLC program (Song et al., 2007, (in press) Methods in Enz. Vol. 433) to achieve separation from interfering compounds. A representative selected reaction monitoring chromatogram of 2,3-dinor-11β-$PGF_{2\alpha}$ in human urine is shown in FIG. 1G. Urinary 2,3-dinor-11β-$PGF_{2\alpha}$ and 11β-$PGF_{2\alpha}$ were both below the limits of detection (about 1 ng/mg creatinine) in mouse urine.

Experimental Example 3

Comparative Levels of Endogenous Metabolites of $PDF_2$ Metabolites

The comparative levels of tetranor PGDM and 2,3-dinor-11β-$PGF_{2\alpha}$ in human urine were 1.5±0.3 ng/mg creatinine and 0.6±0.1 ng/mg creatinine (p<0.01) respectively, while 11β-$PGF_{2\alpha}$ was usually below the limits of detection (FIG.

Figures 2A, 2B, 2C, 2D, 2E:
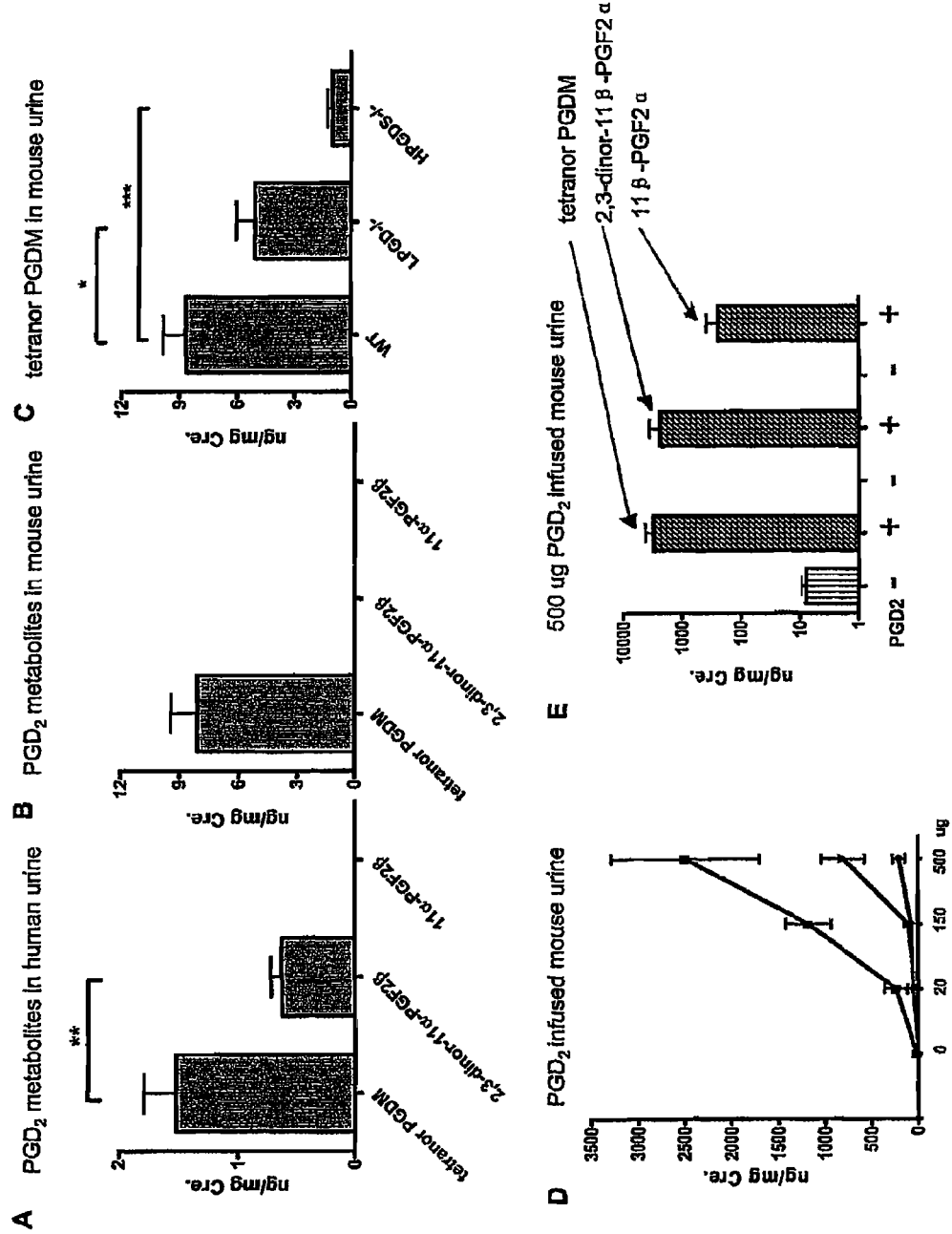
FIGS. 2A-2E are a series of graphs relating to $PGD_2$ metabolites in human and mouse urine.

2A). Tetranor PGDM was the only metabolite detectable in mouse urine at 8.1+1.3 ng/mg creatinine (FIG. 2B).

The comparative disposition of $PGD_2$ was further examined by infusion of exogenous $PGD_2$. All 3 metabolites increased dose dependently in response to the infusion (FIG. 2D). The levels of tetranor PGDM, 2,3-dinor-11β-$PGF_{2\alpha}$ and 11β-$PGF_{2\alpha}$ attained after the maximal dose (500 ug) of $PGD_2$ were 2498±792 ng/mg creatinine, 809±346 ng/mg creatinine and 207±67 ng/mg creatinine, respectively (FIG. 2E). Roughly 3-10% of infused $PGD_2$ was excreted as the tetranor PGDM metabolite in mouse urine. The fractional conversion to each metabolite appeared to be uninfluenced by dose.

Experimental Example 3

Enzymatic Contributions to the Biosynthesis of $PGD_2$

Deletion of either one of the two PGD synthases in mice significantly reduced biosynthesis of $PGD_2$. Tetranor PGDM was suppressed by deletion of L-PGDS from a mean 8.6 ng/mg creatinine to a mean 5.1 ng/mg creatinine ($p<0.05$) and from a mean 8.6 ng/mg creatinine to a mean 1.0 ng/mg creatinine, by deletion of H-PGDS ($P<0.0001$) (FIG. 2C). Deletion of H-PGDS had a significantly greater ($p<0.05$) impact on urinary tetranor PGDM, than did deletion of L-PGDS.

Figures 3A, 3B:
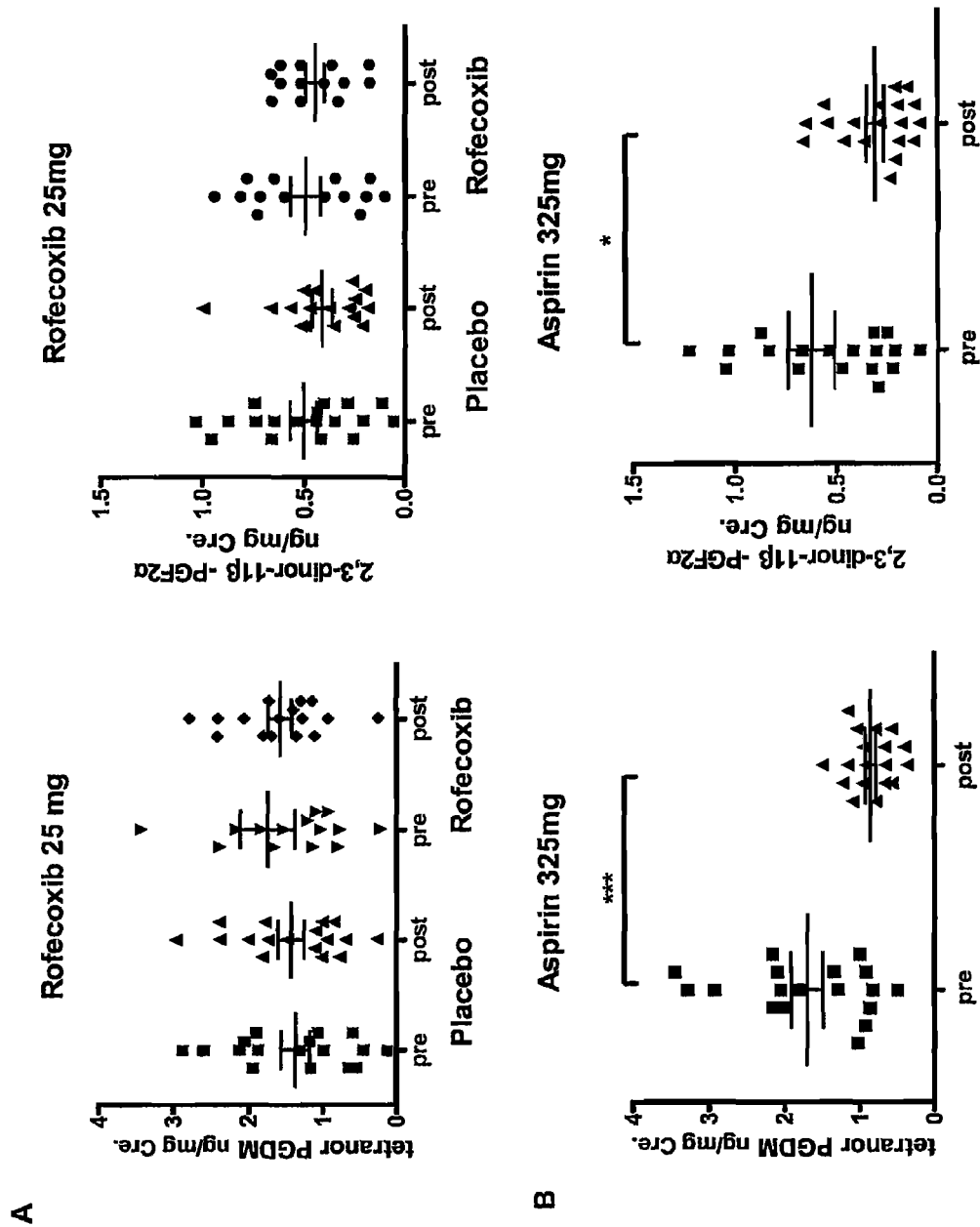
FIGS. 3A and 3B are a series of graphs relating to the effects of selective COX-2 inhibition by rofecoxib and non-selective COX inhibition by aspirin on excretion of major urinary $PGD_2$ metabolites.

The comparative contributions of COX-1 and COX-2 to biosynthesis of $PGD_2$ in humans was addressed by comparing the impact of aspirin at a dose (325 mg) that inhibits both COX isoforms (FitzGerald et al., 1983, J Clin Invest., 71: 676-688) to rofecoxib 25 mg which inhibits selectively COX-2 (Fries et al., 2006, Gastroenterology, 130: 55-64). While rofecoxib failed to depress either tetranor PGDM or 2,3-dinor-11β-$PGF_{2\alpha}$ (FIG. 3A), tetranor PGDM level decreased from 1.71±0.21 ng/mg creatinine to 0.86±0.07 ng/mg creatinine $p<0.001$) and 2,3-dinor-11β-$PGF_{2\alpha}$ decreased from 0.63±0.11 ng/mg creatinine to 0.32±0.04 ng/mg creatinine ($p<0.01$; FIG. 3B) following aspirin.

Experimental Example 4

Evoked Biosynthesis of $PGD_2$

Figures 4A, 4B, 4C, 4D:
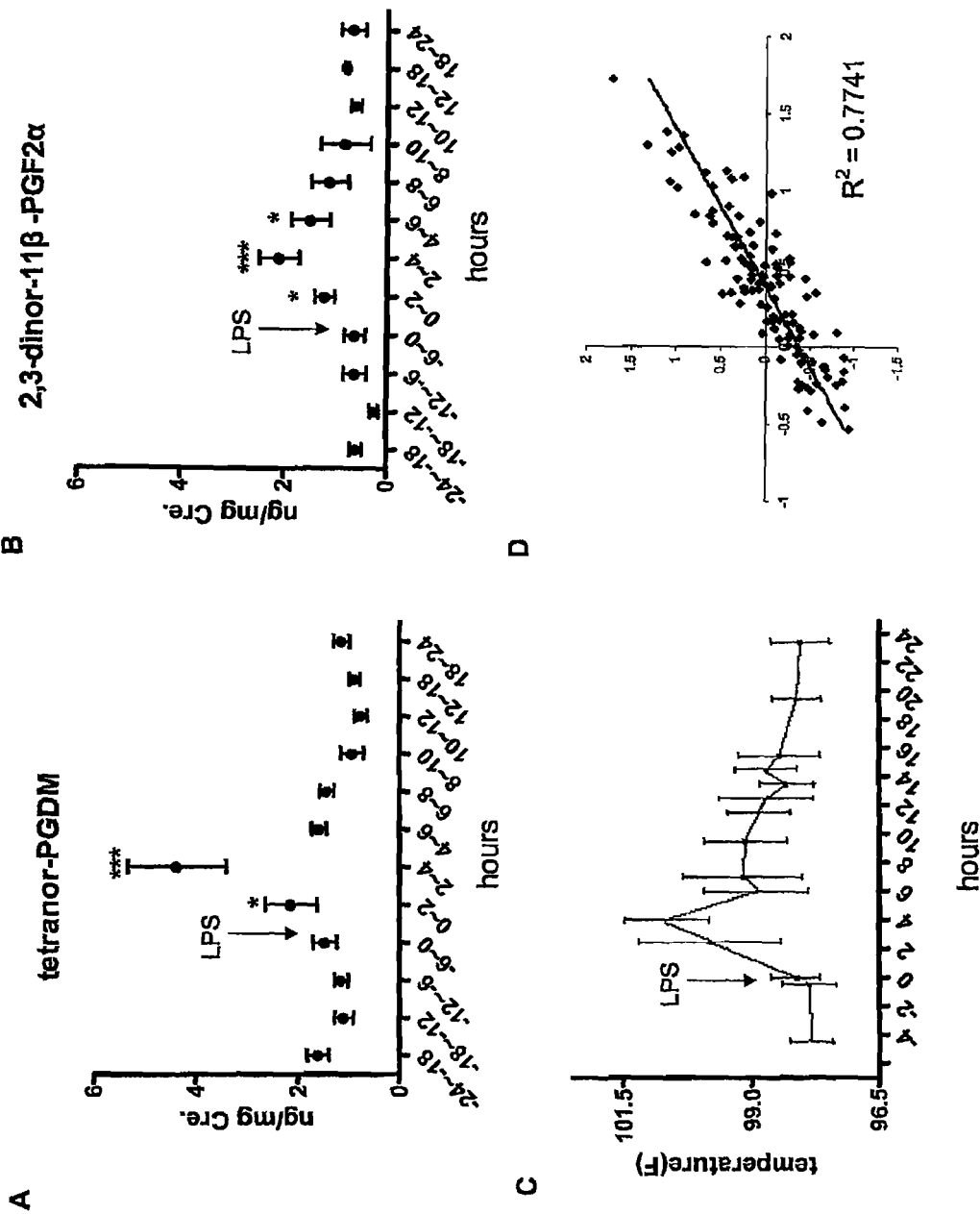
FIGS. 4A-4D are a series of graphs related to LPS-induced increase in excretion of $PGD_2$ metabolites.

LPS evokes a systemic inflammatory response in humans that is accompanied by regulated expression of both COX isozymes ex vivo and augmented biosynthesis of thromboxane A2 and prostacyclin (McAdam et al., 2000, J Clin Invest, 105: 1473-1482). LPS induced a mean increase in both tetranor PGDM (1.49 ng/mg creatinine at baseline to 2.15 ng/mg creatinine at 2 hours and 4.36 ng/mg creatinine at 4 hours after administration) and correspondingly in 2,3-dinor-11β-$PGF_{2\alpha}$ from 0.64 ng/mg creatinine to 1.23 ng/mg creatinine and 2.12 ng/mg creatinine respectively (FIGS. 4A and 4B). The increase in the two metabolites was highly correlated. The peak pyrexial response to LPS (from 97.8° F. to 100.1° F.) occurred about 4 hrs after administration and returned to baseline by 24 hours after LPS administration (FIG. 4C). The alterations in urinary tetranor PGDM and 2,3-dinor-11β-$PGF_{2\alpha}$ in response to LPS occur in a highly coordinated manner (FIG. 4D). Both metabolites fell after the inflammatory response and were not significantly different from basal levels during the resolution phase (8 to 10 hrs after LPS).

Figures 5A, 5B:
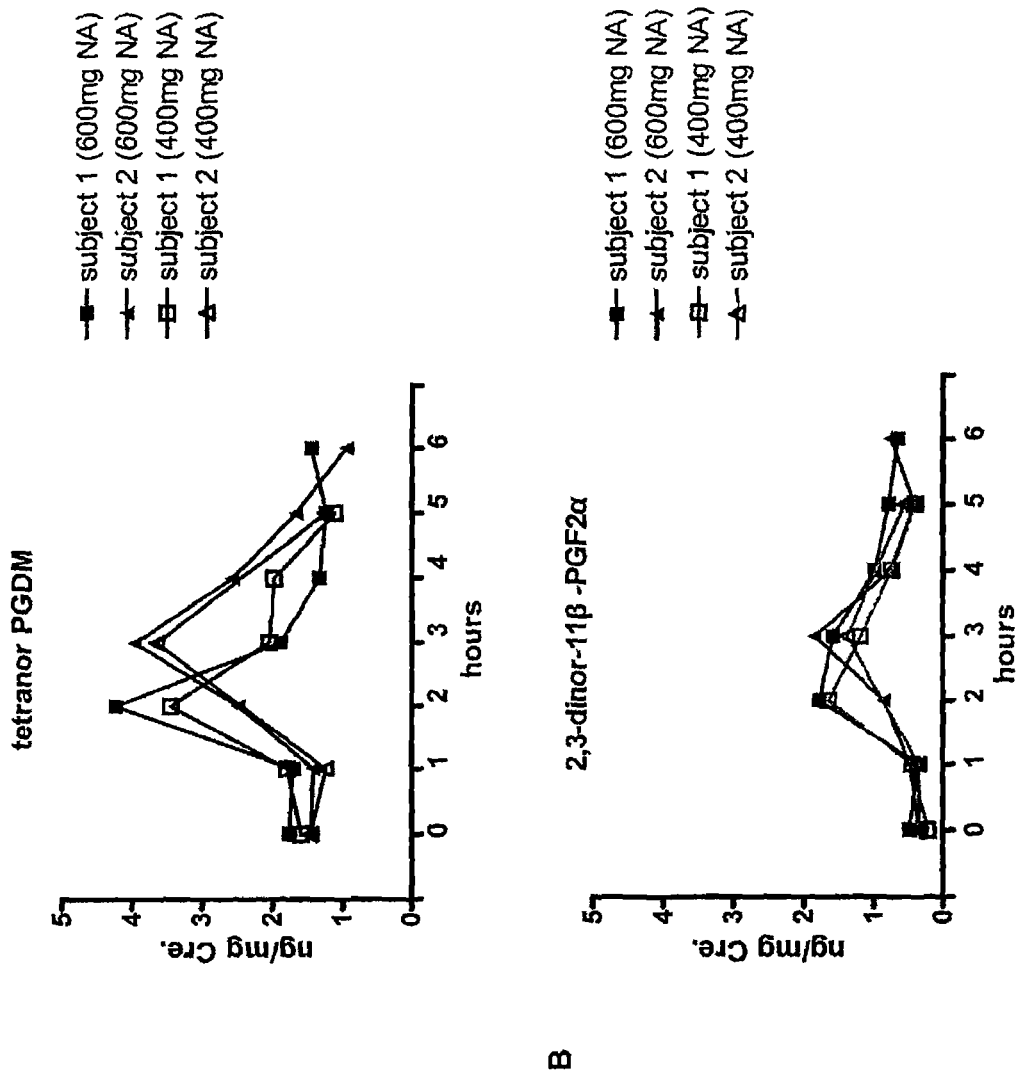
FIGS. 5A and 5B are graphs relating to niacin-evoked urinary PGD$_2$ metabolite excretion.

Oral administration of niacin evoked an intense flush in both volunteers, primarily involving the face and upper part of the body. Flushing was most pronounced during the first hour after dosing and had dissipated after approximately 2-3 hours. Both urinary tetranor PGDM and 2,3-dinor-11β-$PGF_{2\alpha}$ were elevated by niacin (FIGS. 5A and 5B), peaking 2-3 hours and falling to basal levels 5-6 hours after dosing. A relationship between metabolite excretion and the doses of niacin administered was not apparent.

Experimental Example 5

$PGD_2$ and Vascular Injury $PGD_2$ levels were studied in patients undergoing percutaneous transluminal coronary angioplasty (PTCA). PTCA is a common non-surgical treatment for opening obstructed coronary arteries. During PTCA, a balloon-tipped catheter is threaded from an artery in the groin to the trouble spot in the artery of the heart. The balloon is then inflated, thereby compressing the plaque and opening (dilating) the narrowed coronary artery so that blood flow is improved. In some instances, an expandable metal stent is also inserted; stents are wire mesh tubes used to counteract further constriction.

The inclusion and exclusion criteria for participation in the $PGD_2$ level assessment were as follows.

Inclusion:
a. Males and females between the ages of 18-99.
b. Patients with pre-existing coronary artery disease (CAD) admitted for elective Percutaneous Transluminal Coronary Angioplasty (PTCA; common non-surgical treatment for opening obstructed coronary arteries):
   1. Treated with any dose of aspirin (acetylsalicylic acid; ASA) daily for at least 5 days OR
   2. Treated with 81 mg of aspirin daily whose regimen is not changed prior to 24 hours post-procedure, as approved by a physician OR
   3. Treated with an alternative antiplatelet therapy, such as clopidogrel, due to an aspirin hypersensitivity or PMDs preference OR
   4. Treated with an alternative antiplatelet therapy, due to either an aspirin hypersensitivity or PMDs preference, whose regimen is not changed prior to 24 hours post-procedure, as approved by a physician OR
   5. No aspirin therapy at all.
c. Patients presenting to the emergency room (ER) with Acute Coronary Syndrome (ACS) who will have a PTCA.
d. Patients with stable angina or positive stress tests scheduled for a cardiac catheterization.

Exclusion:
a. History of unstable diabetes (Hgb A1c>8 or FBS>200).
b. Uncontrolled hypertension (SBP>180, DBP>100).
c. History of an acute confounding disease as judged on clinical screen that according to the investigator may interfere with interpretation of the study results, or compromise the safety of a potential subject.
d. Patients who have taken NSAIDS or COX-2 inhibitors other than ASA, for at least 10 days prior to PTCA Nineteen (19) subjects scheduled for elective PTCA and/or who presented to the emergency room with acute coronary syndrome and subsequently ordered a PTCA were screened according to the inclusion and exclusion criteria. The studied population included patients on a daily 81 mg aspirin regimen (preferentially inhibits COX-1); patients on a daily 325 mg aspirin regimen (inhibits both COX-1 and COX-2); and patients on a daily alternative antiplatelet regimen.

Urine was collected from each subject at three times. The first urine collection (pre-procedure sample; "Pre") was obtained prior to the dose of the alternative antiplatelet therapy, 81 mg aspirin or 325 mg aspirin, which was administered just before the PTCA. Subjects were taken to the cardiac catheterization lab for their PTCA as scheduled, and a second urine collection that covered the period of the procedure (during-procedure sample; "During") was started, and which lasted approximately 6 hours. After the PTCA procedure, the third and final urine collection (post-procedure sample; "Post") was made, during which urine was obtained for 12 hours. Urine samples were kept at −80° C.

The tetranor PDGM level in each sample was then determined by stable isotope dilution, tandem mass spectrometric quantification, following thawing of the sample. The tetranor PGDM level was normalized to the quantity in milligrams (mg) of urine creatinine.

Figure 6:
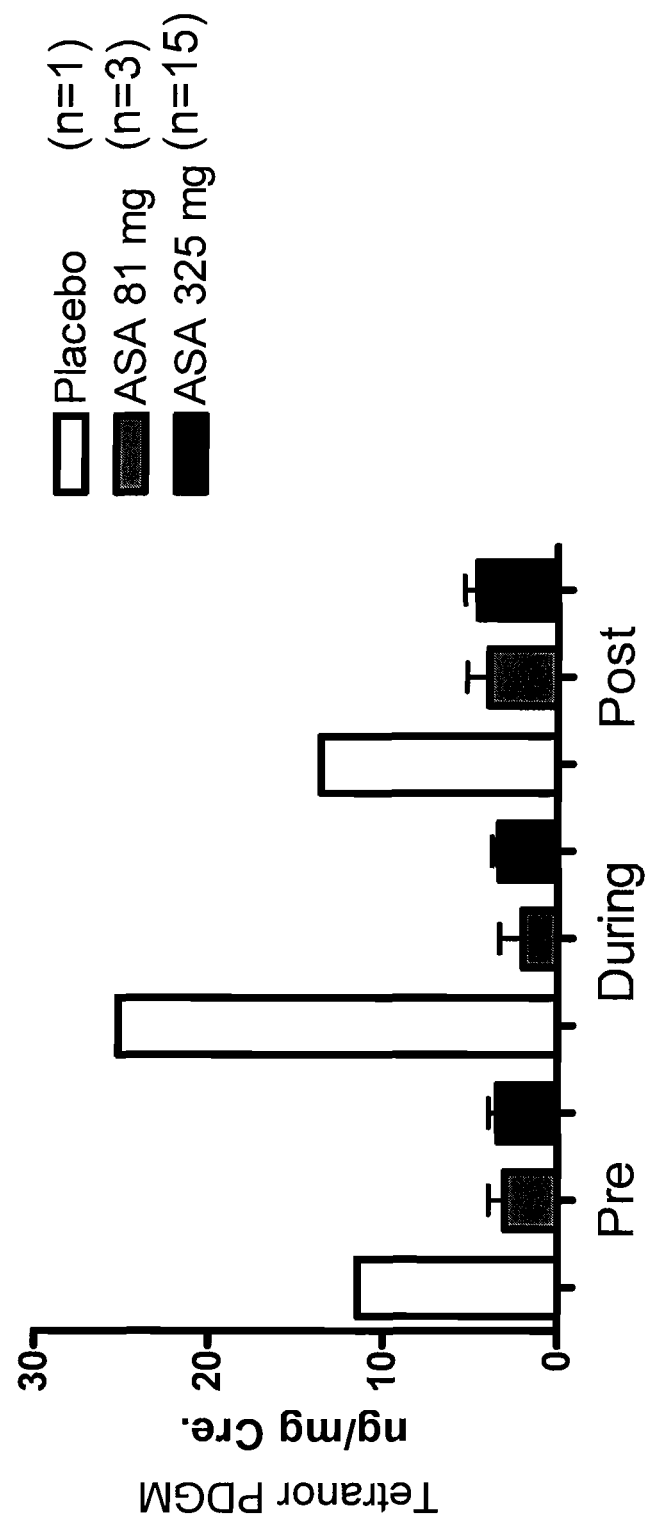
FIG. 6 is a graph relating to urinary tetranor PGDM levels of patients undergoing angioplasty. Pre=sample obtained prior to angioplasty procedure; During=sample obtained during angioplasty procedure; Post=sample obtained after angioplasty procedure. ASA=aspirin. Cre=creatinine.

The data are summarized in Table 1 and depicted in FIG. 6. In the patient (n=1) treated with an alternative antiplatelet regimen (clopidogrel; does not effect prostaglandin formation) and no aspirin, urinary tetranor-PGDM levels increased from 11.5 ng/mg creatinine pre-PTCA procedure to 26.3 ng/mg creatinine during the procedure, then dropped back to 13.1 ng/mg creatinine after the PTCA procedure. In the patients (n=3) on a daily regimen of 81 mg aspirin, urinary tetranor-PGDM level pre-PTCA (2.6 ng/mg creatinine) was suppressed compared to level of that in patient treated with no aspirin. Urinary tetranor-PGDM level did not substantially change during PTCA (1.8 ng/mg creatinine) and after PTCA (3.1 ng/mg creatinine). A similar pattern was observed in the patients treated 325 mg aspirin. Specifically, the pre-PTCA level (2.9 ng/mg creatinine), during-PTCA level (2.8 ng/mg creatinine) and post-PTCA level (3.1 ng/mg creatinine) were substantially the same.

TABLE 1

| | Level of tetranor-PGDM (in ng/mg creatinine) | | |
|---|---|---|---|
| | no aspirin | 81 mg aspirin | 325 mg aspirin |
| Pre-PTCA | 11.5 | 2.6 | 2.9 |
| During-PTCA | 26.3 | 1.8 | 2.8 |
| Post-PTCA | 13.1 | 3.1 | 3.1 |

These data indicate that aspirin suppresses $PGD_2$ levels (compare the no aspirin to the aspirin data). Furthermore, these data suggest that $PGD_2$ is released as a protective reaction. Specifically, during the process of PTCA, $PGD_2$ level increases (see the no aspirin data). Since $PGD_2$ is known to be a vasodilator and, by binding to the DP1 receptor in platelets, can reduce or prevent platelet aggregation, the increase in $PGD_2$ during the PTCA likely counteracts a transient acute vascular injury and/or increased platelet interaction induced by the PTCA procedure. Accordingly, monitoring the level of tetranor PGDM may serve as an indicator of the extent of vascular injury during the procedure. These data also support the use of tetranor PGDM to detect occurrence and/or magnitude of vascular injury, such as acute coronary syndrome, or to monitor the response to vascular injury.

Furthermore, the major peri-procedure adverse affect of PTCA is acute myocardial infarction, which occurs about 5% of the time. Based these data, it appears that the efficacy of aspirin treatment that halves this adverse event rate by suppressing thromboxane, may be countered by the coincident suppression of a cardioprotective prostaglandin, $PGD_2$. Suppression of $PGD_2$ might also represent a particular hazard when combined with niacin in patients at risk of cardiovascular disease. Thus, tetranor PGDM may serve as a biomarker to identify those at higher risk of this adverse effect. Specifically, the extent of tetranor PGDM in a patient could be measured before, during and, optionally, after PTCA and compared to corresponding reference tetranor PGDM levels from patients that did and did not experience an acute myocardial infarction and/or delayed restenosis after PTCA to ascertain if the magnitude of the periprocedural PGDM increase forecasts individuals susceptible to either event.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of detecting whether prostaglandin $D_2$ ($PGD_2$) has been metabolized in an animal, the method comprising the steps of:
   providing a biological sample from an animal, and
   detecting an underivatized tetranor PGDM of Formula I in the biological sample using a method comprising liquid chromatography/tandem mass spectroscopy or an immunoassay

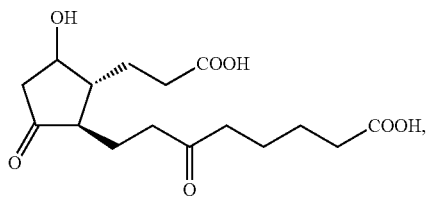

wherein, if the underivatized tetranor PGDM of formula I is detected in the biological sample of the animal, $PGD_2$ has been metabolized in the animal.

2. The method of claim 1, further comprising isolating the underivatized tetranor PGDM of formula I from the sample.

3. The method of claim 1, wherein the biological sample is urine.

4. The method of claim 2, further comprising quantifying the amount of the isolated underivatized tetranor PGDM in the sample.

* * * * *